(12) United States Patent
Patrick, III et al.

(10) Patent No.: US 9,247,729 B2
(45) Date of Patent: Feb. 2, 2016

(54) SYSTEMS AND METHODS FOR PRESERVING A HUMAN ORGAN FOR TRANSPLANTATION

(75) Inventors: Charles H. Patrick, III, Morris, AL (US); Danny M. Ondler, Oronoco, MN (US); Patrick Delorme, Chaponost (FR)

(73) Assignee: INSTITUT GEORGES LOPEZ, Saint Didier Au Mont D'Or (FR)

( * ) Notice: Subject to any disclaimer, the term of this patent is extended or adjusted under 35 U.S.C. 154(b) by 1072 days.

(21) Appl. No.: 12/475,225

(22) Filed: May 29, 2009

(65) Prior Publication Data

US 2010/0304352 A1 Dec. 2, 2010

(51) Int. Cl.
 C12M 1/00 (2006.01)
 A01N 1/00 (2006.01)
 A01N 1/02 (2006.01)

(52) U.S. Cl.
 CPC .................................. *A01N 1/0247* (2013.01)

(58) Field of Classification Search
 CPC ... A01N 1/0242; A01N 1/021; A01N 1/0247; C12M 21/08
 See application file for complete search history.

(56) References Cited

U.S. PATENT DOCUMENTS

| | | | |
|---|---|---|---|
| 3,753,865 A | 8/1973 | Belzer et al. | |
| 3,995,444 A | 12/1976 | Clark et al. | |
| 4,260,079 A * | 4/1981 | Cary et al. | 222/209 |
| 4,417,861 A * | 11/1983 | Tolbert | 417/315 |
| 5,157,930 A | 10/1992 | McGhee et al. | |
| 5,586,438 A | 12/1996 | Fahy | |
| 5,888,186 A * | 3/1999 | Trumble et al. | 600/16 |
| D453,828 S | 2/2002 | Brassil et al. | |
| D470,594 S | 2/2003 | Brassil et al. | |
| 6,977,140 B1 | 12/2005 | Owen et al. | |
| 7,238,165 B2 * | 7/2007 | Vincent et al. | 604/6.11 |
| 7,504,201 B2 | 3/2009 | Taylor et al. | |
| 8,133,042 B2 * | 3/2012 | Yajima | 417/473 |
| 8,540,499 B2 * | 9/2013 | Page et al. | 417/437 |
| 2006/0160204 A1 * | 7/2006 | Hassanein et al. | 435/284.1 |
| 2008/0227189 A1 * | 9/2008 | Bader | 435/289.1 |
| 2008/0262288 A1 | 10/2008 | Tatum et al. | |
| 2009/0275875 A1 * | 11/2009 | Liebing | A61M 1/3632 604/6.09 |

FOREIGN PATENT DOCUMENTS

EP 0 347 932 A1 12/1989

OTHER PUBLICATIONS www.organ-recovery.com/home.php—Organ Recovery Systems, LifePort, Jan. 2009.

* cited by examiner

*Primary Examiner* — Nathan Bowers
(74) *Attorney, Agent, or Firm* — Heslin Rothenberg Farley & Mesiti P.C.; Victor A. Cardona, Esq.

(57) ABSTRACT

A perfusion pump system for providing perfusate to an organ of a human body includes an actuator coupled to a pump to provide an actuating force to the pump. The pump includes an outlet for providing a perfusate to an organ coupled to the pump and an inlet for receiving the perfusate. The pump is configured to provide a pulsatile pumping force to the perfusate via a pumping stroke in response to the actuating force. The pumping stroke is followed by a return stroke. The pumping stroke causes the pump to collapse to force a flow of the perfusate through the outlet to the organ. The pump collapses in the direction of the flow of the perfusate. The return stroke allows the perfusate to enter the pump through the inlet and the return stroke of ways providing the perfusate through the outlet.

1 Claim, 9 Drawing Sheets

SYSTEMS AND METHODS FOR PRESERVING A HUMAN ORGAN FOR TRANSPLANTATION

TECHNICAL FIELD

This invention relates, in general, and, in particular, to systems and methods for organ preservation, evaluation, and transport.

BACKGROUND ART

The transplantation of an organ from one person to another often requires that the organ be evaluated and preserved from the time of its removal from a body (e.g., a deceased human body) and transplantation into a second body (e.g., a recipient). Once the organ has been removed, it is generally preserved for a short period by washout with a standard organ preservation solution and aseptic storage on ice. The organ, depending on the protocol of the center involved, can be preserved and transported prior to transplantation on a system which holds the organ in a container, cools the organ (e.g., to about 3-5 degrees C), and provides the organ with a perfusate to continually washout and preserve the organ. The system may also provide oxygenated perfusate and precursors for energy production to the organ to aid in its preservation. The system is further designed to mimic human perfusion physiology whereas a pulsatile pump replicates the pumping action of the human heart by forcing (or ejecting) a stroke volume of perfusate under an established pressure set by the operator. This set pressure is, in effect, the same type of pressure generated by the human heart in the contraction phase (or systolic phase). As the pump resets or recoils, the pressure decreases to a diastolic (or resting) pressure. A pressure monitoring system in the device measures both the systolic, diastolic and also calculates a mean pressure for evaluation by the operator.

It is important to note that after the removal of an organ (e.g., kidney) from a human body, the arteries of the organ may become vasoconstricted due to the cold preservation solution used to washout the organ during the recovery procedure from the donor such that it is necessary to provide a pulsed force to the arteries to re-open them prior to the organ being transplanted into a second human body. Such a pulsed force is believed to be most effective when initially delivered in a low frequency, low volume, low pressure system. The force can be gradually increased during the preservation period prior to transplantation of the organ. The perfusate is therefore provided in a pulsed manner by a pump which is designed to deliver the perfusate within a set of controlled specifications. An organ may only be able to tolerate a certain pressure and/or volume of perfusate from such pump at a given time. The pump specifications must be monitored because if the pressure or volume exceeds a set pressure or volume threshold, damage may be sustained to the organ.

With this background in mind, a need exists for a system and method to preserve an organ prior to transplantation which includes a pump that may be regulated to inhibit damage to an organ due to excess pressure, fluid volume, or temperature such that the organ is preserved and is not damaged while being preserved for transplantation.

SUMMARY OF THE INVENTION

The present invention provides, in a first aspect, a perfusion pump system for providing perfusate to an organ of a human body which includes an actuator coupled to a pump to provide an actuating force to the pump. The pump includes an outlet for providing a perfusate to an organ coupled to the pump and an inlet for receiving the perfusate. The pump is configured to provide a pulsatile pumping force to the perfusate via a pumping stroke in response to the actuating force. The pumping stroke is followed by a return stroke. The pumping stroke causes the pump to collapse to force a flow of perfusate through the outlet to the organ. The pump collapses in the direction of the flow of the perfusate. The return stroke allows perfusate to enter the pump through the inlet and the return stroke avoids providing perfusate through the outlet.

The present invention provides, in a second aspect, an organ preservation system which includes a pump coupled to an actuator configured to provide a force to the pump. A cassette is configured to hold an organ and is coupled to the pump. The pump includes an outlet for providing a perfusate to an organ received in the cassette and coupled to the pump and an inlet for receiving the perfusate returning from the cassette. The pump is configured to provide a pulsatile pumping force to the perfusate via a pumping stroke followed by a return stroke. The pumping stroke causes the pump to collapse to force a flow of perfusate through the outlet to the organ. The pump collapses in the direction of the flow of the perfusate. The return stroke allows perfusate to enter the pump through the inlet and the return stroke avoids providing perfusate through the outlet.

The present invention provides, in a third aspect, a method for preserving an organ which includes an actuator providing an actuating force to a pump to cause a pumping stroke to cause a collapse of the pump to send a flow of a perfusate from the pump through an outlet of the pump to an organ received in a cassette. The pump collapses in a direction of the flow of the perfusate. The actuator retreats away from the pump to remove the actuating force from the pump. The pump returns toward a starting position and receives perfusate through an inlet of the pump while avoiding sending fluid through the outlet.

BRIEF DESCRIPTION OF THE DRAWINGS

The subject matter, which is regarded as the invention, is particularly pointed out and distinctly claimed in the claims at the conclusion of the specification. The foregoing and other objects, features, and advantages of the invention will be apparent from the following detailed description of preferred embodiments taken in conjunction with the accompanying drawings in which:

DETAILED DESCRIPTION

Figure 1:
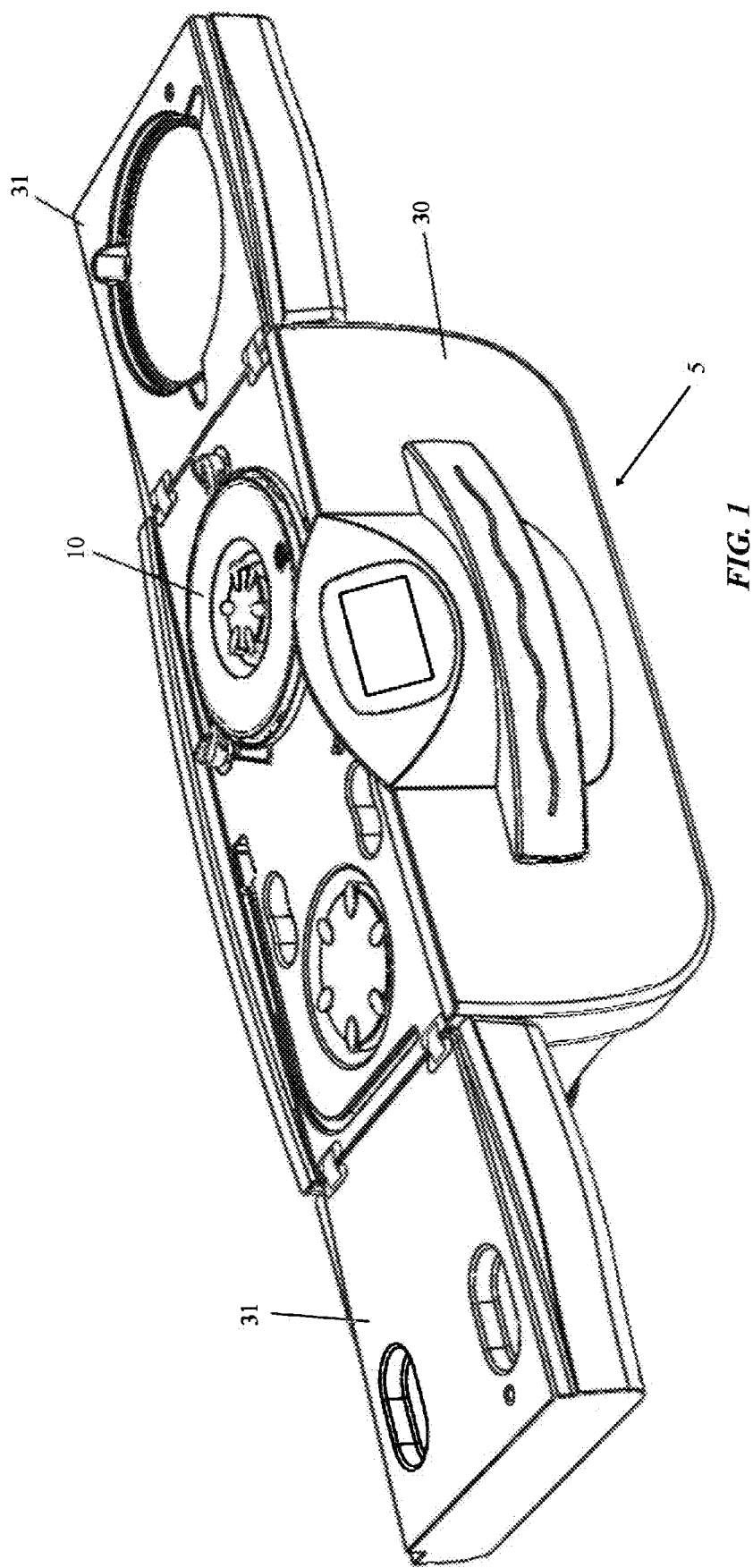
FIG. 1 is a perspective view of an organ preservation system in accordance with the present invention.
Figure 2:
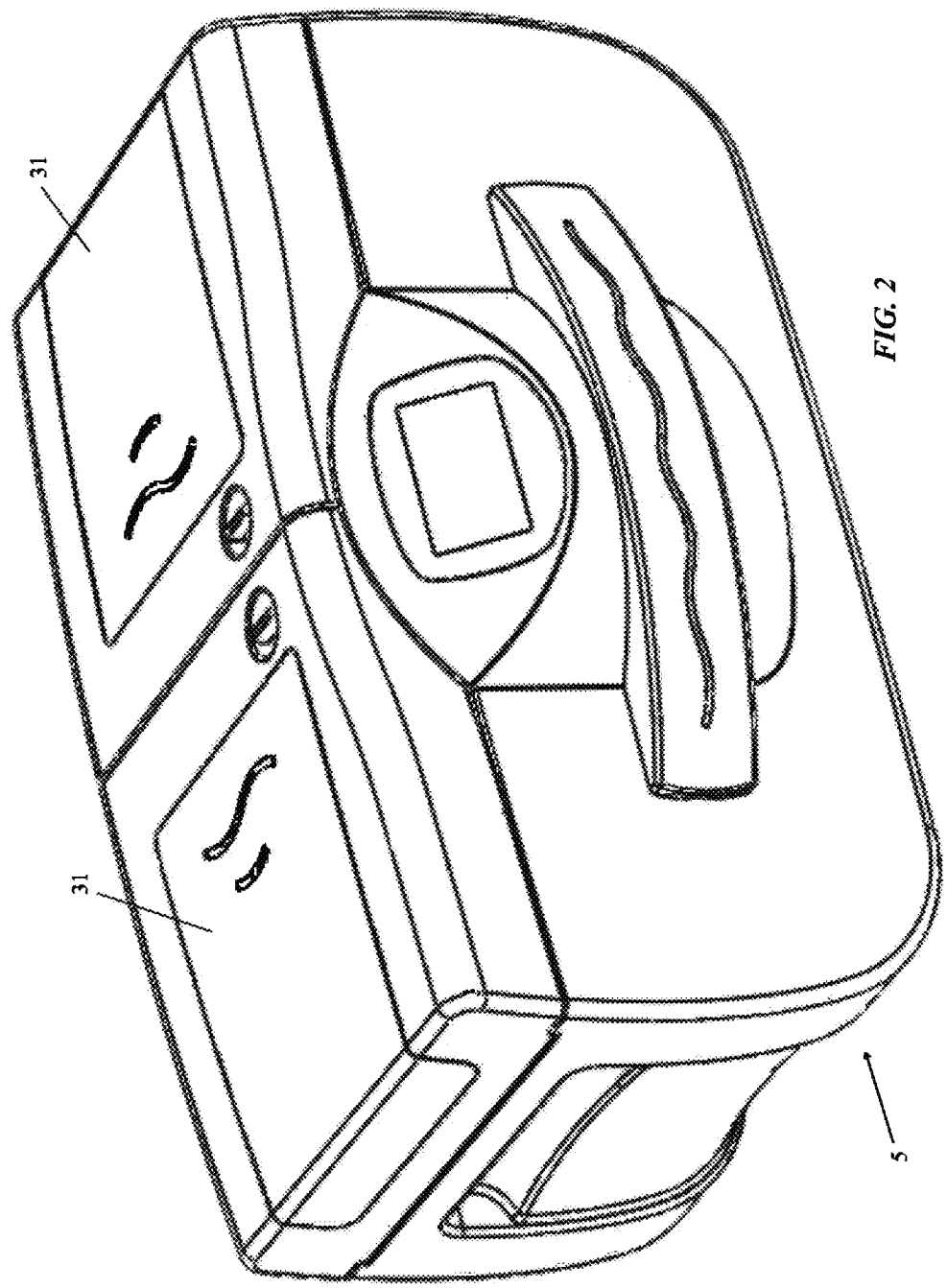
FIG. 2 is a perspective view of the system of FIG. 1 with top doors thereof closed.

In accordance with the principles of the present invention, systems and methods for preserving organs for transplantation are provided.

As depicted in FIGS. 1, 2, 3 and 9, an organ preservation system 5 includes a cassette 10 for holding an organ 20. The cassette is inserted and attached to a housing 30 such that the cassette is designed to be removed and discarded after each use and substituted with a new cassette to ensure that a new sterile cassette may be utilized for each organ. Housing 30 includes openable doors 31 which may be used as a work surface (e.g., to place an organ or surgical instruments thereon) when in the position depicted in FIG. 1 and which may provide some insulative effect (e.g., to cassette 10) when in the position depicted in FIG. 2.

Figure 3:
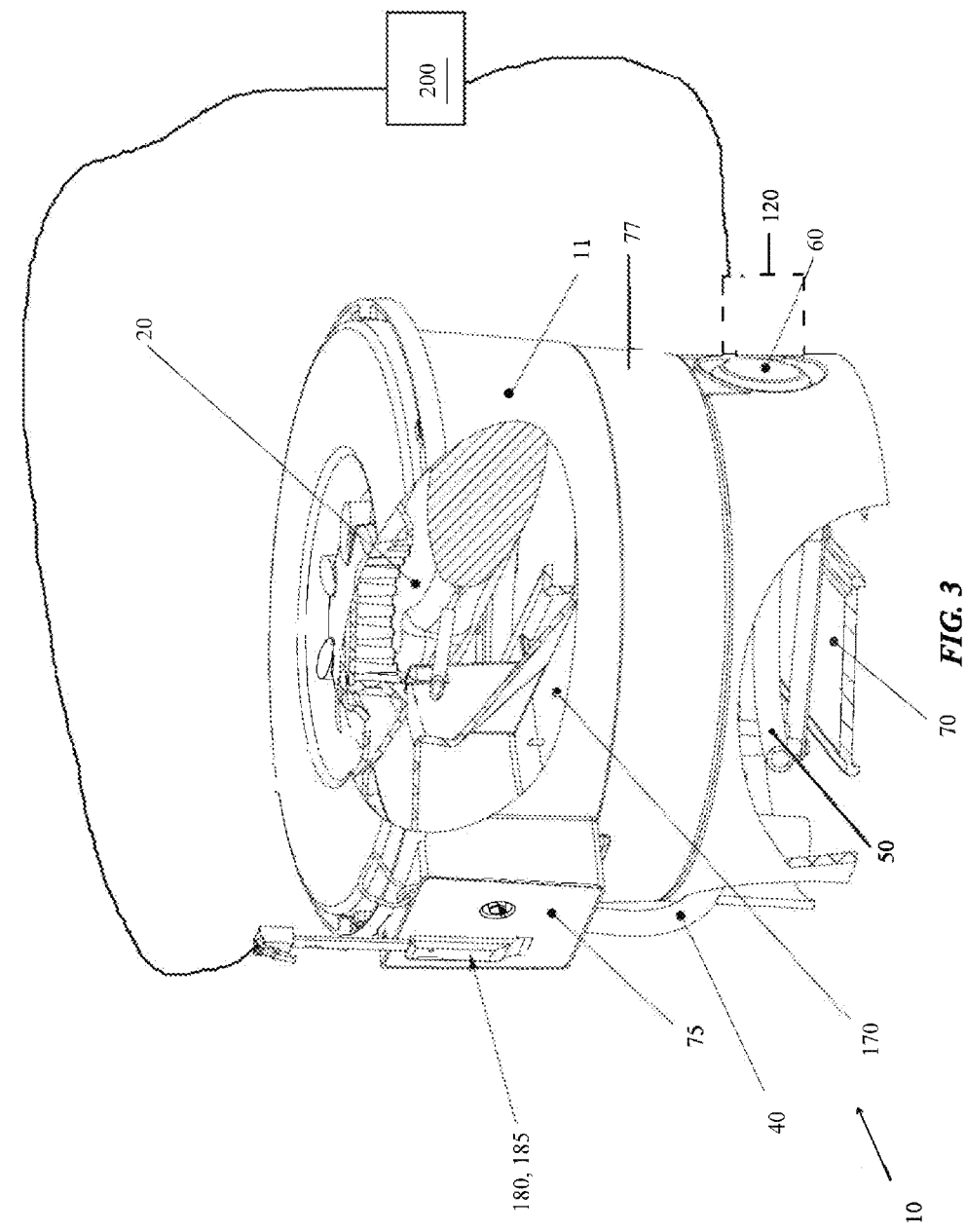
FIG. 3 is a perspective partial cross-sectional view of a cassette of the system of FIG. 1.
Figure 9:
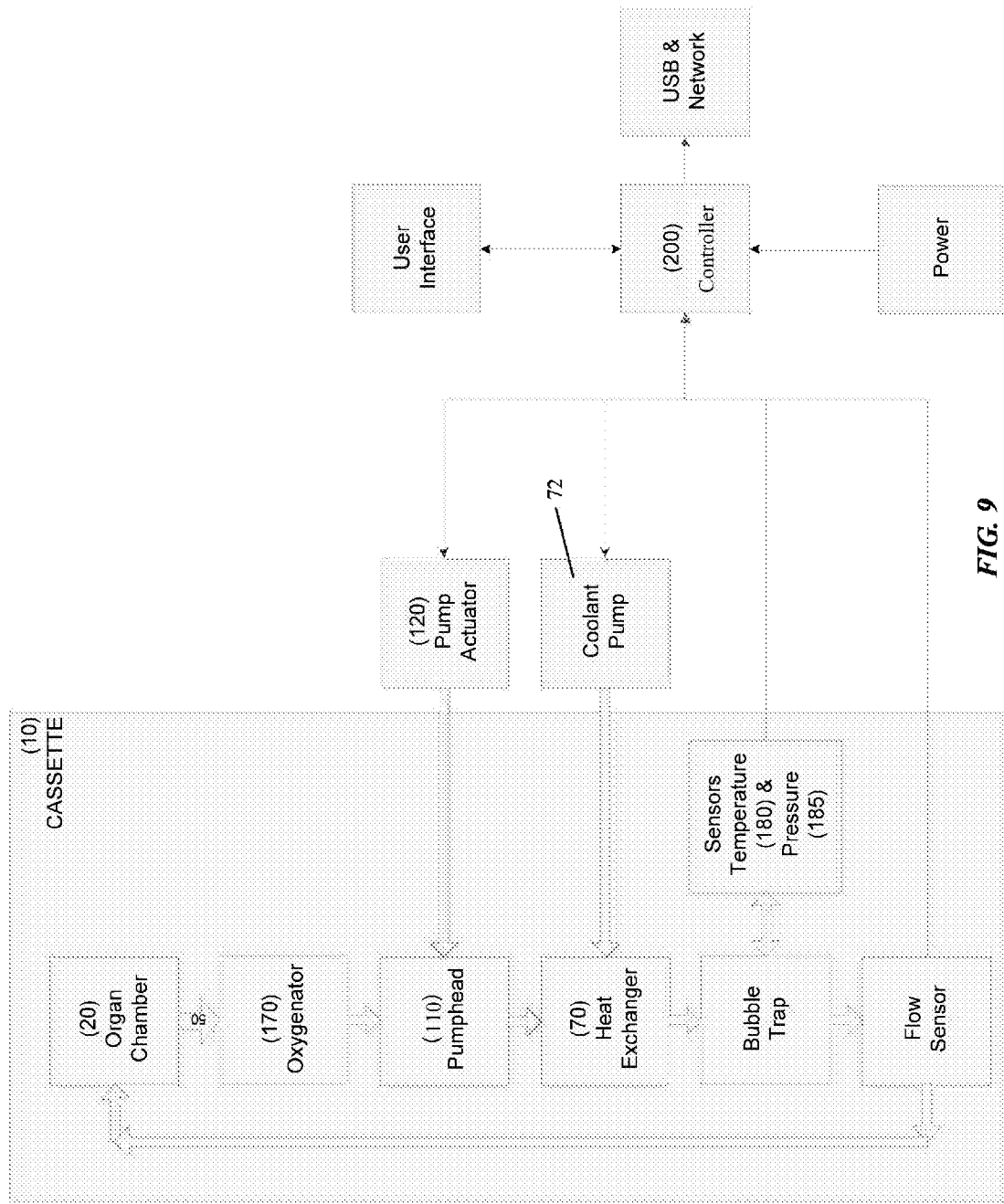
FIG. 9 is a block diagram of the system of FIG. 1.

An organ chamber 11 of cassette 10 may be connected by an inflowing conduit 40 and an outflowing conduit 50 to a pump assembly 60. Conduit 50 flows from pump assembly 60 through a heat exchanger 70 to control a temperature of a fluid (e.g., perfusate) flowing from pump assembly 60 to organ chamber 11. The heat exchanger may have its temperature, and that of the fluid flowing through it, controlled by being immersed in, abutting, or otherwise thermally coupled to a temperature controlling (e.g., cooling) fluid, such as an ice-water bath, or a pumped heat transfer fluid via a coolant pump 72. After exiting the heat exchanger, the conduit connects to a bubble trap 75 to allow any air bubbles to be trapped prior to conduit 50 connecting to organ chamber 11 and organ 20 as depicted in FIGS. 3 and 9. Alternatively, conduit 40 could flow through heat exchanger 70 prior to the perfusate entering pump assembly 60.

Figure 4:
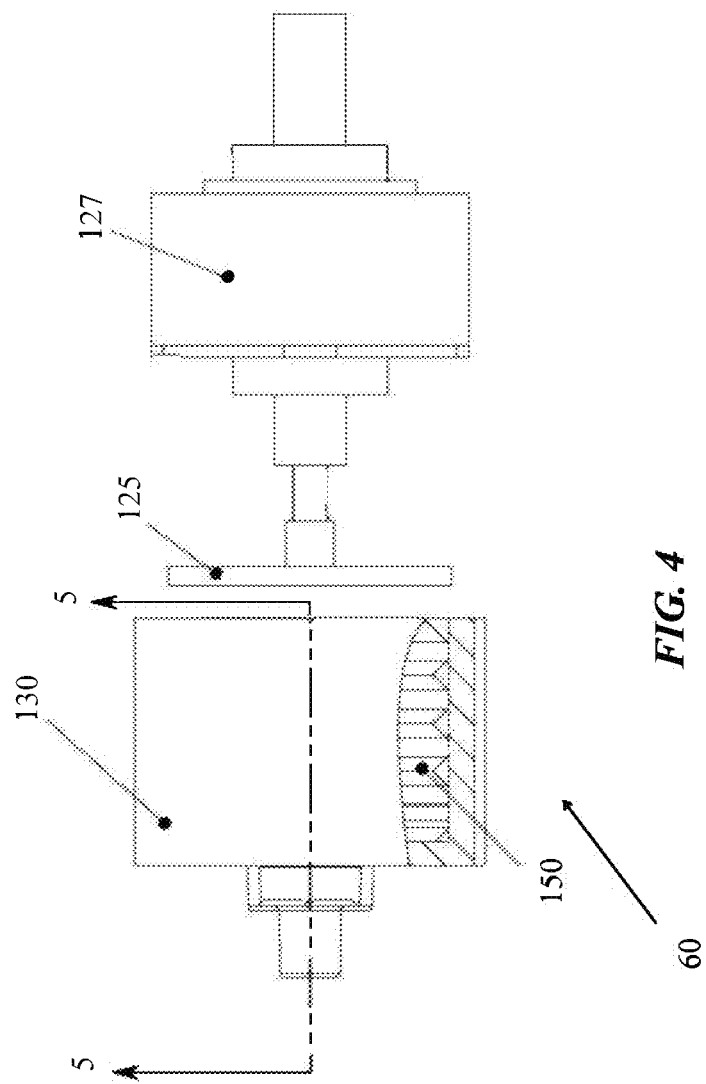
FIG. 4 is a top view of a perfusate pump assembly of the system of FIG. 1 in partial cross-section.
Figure 5:
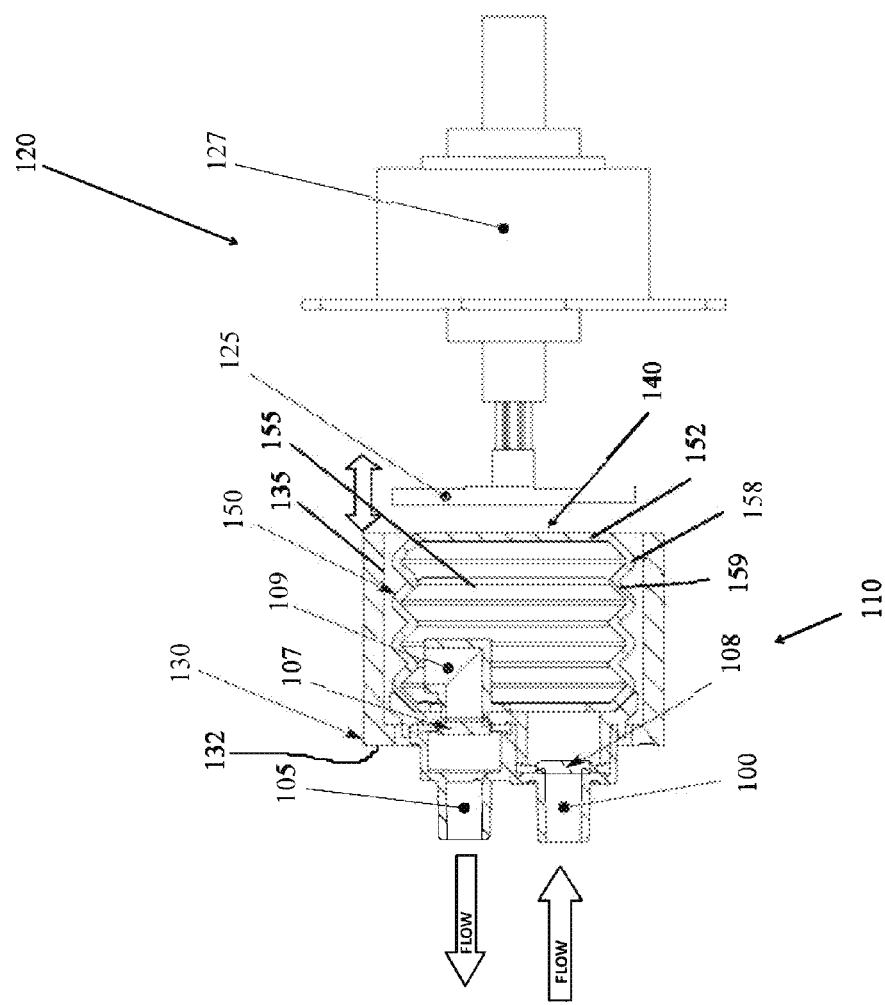
FIG. 5 is side view of the pump assembly of FIG. 4 in partial cross-section along lines 5-5 of FIG. 4.

The fluid may flow by gravity from organ chamber 11 through inflowing conduit 40 to an oxygenating device 170 (e.g., an oxygenating membrane) in an oxygenation chamber 77 for providing oxygen to the perfusate and then to an inlet 100 of a pump 110 of pump assembly 60 as depicted in FIGS. 4-5. The fluid may be sent or returned to organ chamber 11 by a pumping force provided by pump 110 such that the fluid flows through an outlet 105 to conduit 50 to organ chamber 11.

Figure 6:
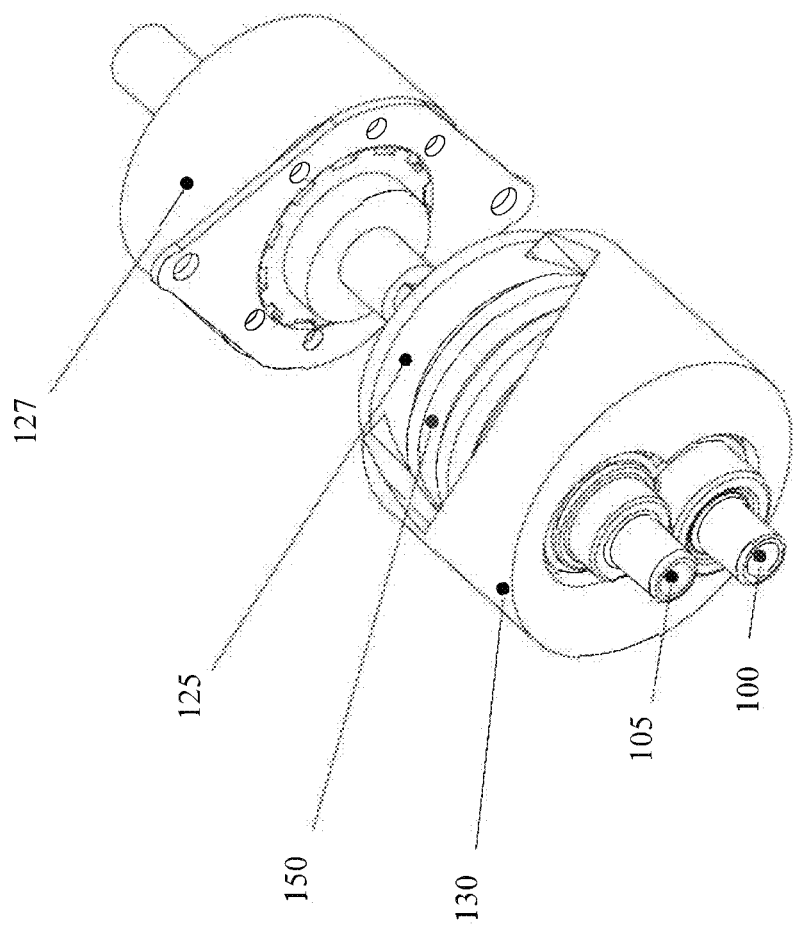
FIG. 6 is a perspective view of the pump assembly of FIG. 4 in partial cross-section.

Pump assembly 60 includes pump 110 and an actuator 120 as depicted in FIGS. 4-6. Pump 110 includes a housing 130 having an inner surface 135 defining a cavity 140 receiving a pump body 150. Pump body 150 may have an internal cavity 155 which receives a fluid (e.g., perfusate) to be pumped. The fluid may exit outlet 105 in response to a linear force from actuator 120 on an actuator end 152 of pump body 150 of pump 110 toward an inlet/outlet end 132. Outlet 105 may include a one-way valve 107 such that fluid may only flow throughout outlet 105 toward cassette 10. Similarly, inlet 100 may include a one-way valve 108 such that fluid may only flow therethrough toward internal cavity 155. The inlet and outlet may also be substantially parallel to one another and to a longitudinal dimension of pump 110 and actuator 120. The axial alignment of the outlet and actuator 120 may provide for efficient transmission of a force provided by actuator 120 to the fluid through outlet 105. An elbow 109 inhibits the passing of air bubbles from internal cavity 155 through outlet 105.

Actuator 120 may be any type of actuator (e.g., a hydraulic or pneumatic piston, or electric linear motor) which provides a force such that pump body 150 may decrease in size (e.g., collapse) to force any fluid (e.g., a perfusate) therein through outlet 105 toward cassette 10. A forcing plate 125 of actuator 120 may contact actuator end of pump body 150 to provide the force thereto. After forcing plate 125 has reached a desired position within cavity 140, the plate may stop and reverse direction toward an actuator body 127 of actuator 120. Any force provided from actuator 120 to pump body 150 may thus reach a point where a zero force is provided to pump body 150 prior to a retraction of forcing plate 125 toward actuator body 127. This reduction of force to zero and retraction of forcing plate 125 in an opposite direction relative to a forcing direction creates a repeatable pulsatile force (i.e. by repeated strokes of forcing plate 125) which mimics the force which may be provided to an organ (e.g., a kidney) in the human body. This mimicking of the natural condition promotes the preservation of an organ received in a cassette and coupled to pump 110.

Pump body 150 may have an accordion-shape as depicted in FIGS. 4-5. Specifically, pump body may include a outer surface which undulates, convolutes or zig zags from a maximum outer diameter 158 to a minimum outer diameter 159 and back to the maximum outer diameter again throughout an axial length of pump body 150. Pump body 150 may thus fold similar to an accordion upon pressure being applied thereto by actuator 120. Pump body 150 may be formed of silicone or another material(s) which is resilient and flexible enough to absorb any stresses that may be provided in the closed loop system of fluid circulated from the pump to the cassette and back. This ability to absorb a stress or shock inhibits damage to an organ received in the cassette and coupled to the pump by allowing such stress to be absorbed by pump body 150. Such stresses could be the result of a pressure or flow rate which exceeds that which an organ is ready to tolerate at a particular time. Housing 130 may be formed of a material more rigid than the pump body, e.g., steel or a rigid plastic.

As depicted in the figures, pump body 150 may be received in pump housing 130 which may be rigid in contrast to the resilient and flexible pump body. As described, pump body 150 is formed as an accordion-shape and has outer diameter portions at a maximum outer diameter 158 and minimum diameter portions at minimum outer diameter 159. The minimum diameter portions may expand toward inner surface 135 to absorb the stresses (e.g., an overpressure within a conduit due to an organ not being able to tolerate a flow rate or pressure) described above without causing damage to pump body 150 or an organ coupled thereto.

As indicated above, forcing plate 125 may provide a force (i.e., a pumping stroke) to pump body 150 followed by a retraction (i.e., a return stroke) thereof in an opposite direction. After forcing plate 125 has stopped and reversed direction toward actuator body 127, pump body 150 may be sufficiently resilient such that it returns to its starting position, i.e., expands in a direction toward the retreating forcing plate 125, without being attached to, and pulled by, forcing plate 125. However, the return of pump body 150 to the starting position may be aided by the elevation of the cassette above pump body 150 thereby utilizing gravity to promote fluid flow through inlet 100 to cavity 155 of pump body 150 thereby promoting such retraction toward actuator 120.

Cassette 10 may also include temperature sensor(s) 180 and pressure sensor(s) 185 for monitoring the temperature and pressure of organ chamber 11 of cassette 10. The sensors may be coupled to a controller 200, and controller may be coupled to actuator 120 (both depicted in FIG. 3 for illustrative purposes but being part of housing 30 and not cassette 10) to allow a pumping rate to be controlled (e.g., to control a pressure, timing, flow rate, and/or volume of perfusate) by controller 200 based on the temperature and pressure within organ chamber 11. For example, the controller may control the movement of actuator 120 to control a pumping rate of pump body 150 to best preserve an organ (e.g., a kidney) by incrementally increasing a pulsed pumping rate of perfusate to the organ. Such incremental increase in pumping may facilitate the opening of any closed veins or blood vessels in the organ. Such a controller may be mechanical or electronic and may be regulated (e.g., programmed) by a user. Such electronic controller could be a personal computer running the WINDOWS operating system or another such operating system as will be known by those skilled in the art, or the controller could be a mainframe computer, server, hand held computer or any such computing unit as would be known by one skilled in the art.

Figure 7:
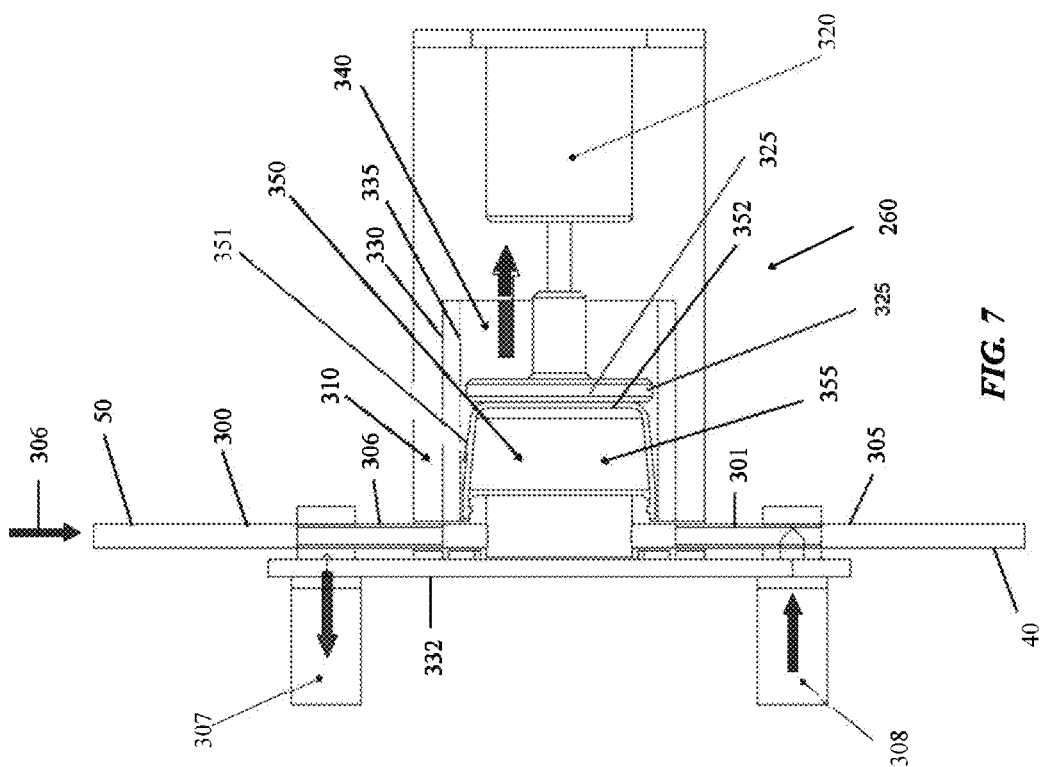
FIG. 7 is a side-cross-sectional view of another embodiment of a perfusate pump in accordance with the present invention.
Figure 8:
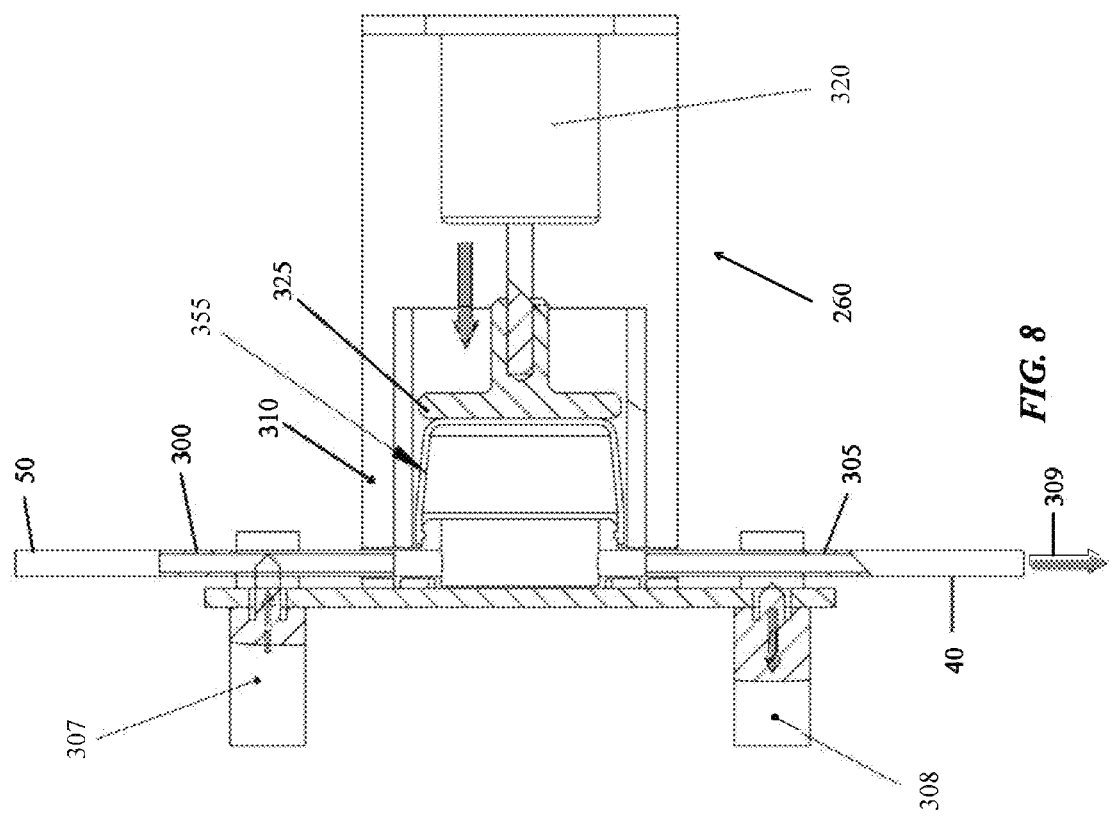
FIG. 8 is a side cross-sectional view of the pump of FIG. 7 showing movement thereof in an opposite direction relative to FIG. 7.

In another example depicted in FIGS. 7-8, a pump assembly 260 may replace pump assembly 60 in system 5. Pump assembly 260 includes a pump 310 and an actuator 320, which may be similar or identical to actuator 120, as depicted in FIGS. 7-8. Pump assembly 260 includes a housing 330 having an inner surface 335 defining a cavity 340 receiving a pump body 350. Pump body 350 may have an internal cavity 355 which receives a fluid (e.g., perfusate) to be pumped. Cavity 355 may be connected to an outlet 305 and may be connected to an inlet 300. The fluid may exit outlet 305 in response to a linear force from actuator 320 toward a supporting plate 332 on an opposite end of pump 310.

Outlet 305 may include a one-way valve or clamp 308 such that fluid may only flow through outlet 305 toward organ chamber 11 of cassette 10. Similarly, an inlet 300 may include a one-way valve or clamp 307 such that fluid may only flow therethrough toward internal cavity 355 from organ chamber 11 of cassette 10. The inlet and outlet may also be substantially parallel to one another and allow flows in opposite directions relative to each other, along with being substantially perpendicular to a longitudinal dimension of pump 110 and actuator 120.

The inlet and outlet provide for fluid communication, and fluid flow, between cavity 355 and organ chamber 11. For example, an arrow 306 in FIG. 7 indicates fluid coming from organ chamber 11 through inlet 300 past clamp 307 to cavity 355 as plate 352 retracts fluid actuator 320. During such retraction clamp 308 is closed to prevent fluid from exiting outlet 305. In contrast, as depicted in FIG. 8, inlet 300 is closed by clamp 307 to inhibit flow from organ chamber 11 to internal cavity 355 while outlet 305 is open (i.e., not closed by clamp 308) to allow fluid to flow from internal cavity 355 through outlet 305 to organ chamber 11 (i.e., in a direction of an arrow 309).

As depicted in the figures, pump body 350 may be received in pump housing 330 which may be rigid in contrast to the resilient and flexible pump body. Pump body 350 may be formed of flexible silicone and have a substantially trapezoidal cross-sectional shape when it is in an uncompressed position as depicted in FIGS. 7-8. An outer surface 351 of pump body 350 tapers toward a forcing plate 325 leaving a space along an outer perimeter thereof between the pump body and inner surface 335. This allows the expansion of outer surface 351 of pump body 350 into such space if necessary due to a stress without causing damage to pump body 350 or an organ coupled thereto within system 5 when pump assembly 260 is incorporated therein.

As indicated above, forcing plate 325 may provide a force to pump body 350 followed by a retraction thereof in an opposite direction. Forcing plate 325 may not be attached to pump body 350 and pump body 350 may return to a starting position separately from forcing plate 325 in response to cavity 355 receiving fluid (i.e., perfusate) as it returns from organ chamber 11 due to a force of gravity on the fluid causing the fluid to flow through inlet 300 to cavity 355. In another example, a forcing plate end 352 of pump body 350 may be connected to forcing plate 325 such that forcing plate 325 may aid movement of end 352, and thus pump body 350, toward actuator 320 when forcing plate 325 retracts toward actuator 320.

As will be understood by one skilled in the art of perfusion, the pump bodies (e.g., pump body 150 and pump body 350) described above may be formed of various materials (e.g., silicone, SEBS, elastomeric thermoplastic) which are resilient such that any stresses applied to the systems (e.g., system 5) in which the pump assemblies are a component of may be absorbed by the pump bodies. Such pump bodies in the housings in which they are received may also be formed of various shapes such that the pump bodies may absorb stresses by expanding in response to such stresses (e.g., into a gap or space between such a pump body 150 and a housing) Further, the pump bodies may be formed of materials (e.g., silicone, SEBS, elastomeric thermoplastic) which maintain a substantially constant temperature in response to multiple pulsed applications (e.g., 60 strokes/min) of force (e.g. by an actuator). For example, the pump bodies avoid substantially increasing in temperature due to the repeated application of force thus providing increased energy efficiency relative to prior art devices which generated heat in response to repeated applications of force thereto. The pump body may also be formed of a material (e.g., silicone or any thermoplastic elastomer, which does not vary much in mechanical characteristics at low temperatures) which is elastically deformable such that it elastically returns to a start position after the release of a pumping force applied thereto (e.g., by an actuator).

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the following claims.

The invention claimed is:
1. An organ preservation system comprising:
  a cassette configured to hold an organ, said cassette coupled to a pump;
  said pump comprising an outlet for providing a perfusate to the organ when the organ is received in said cassette and coupled to said pump and an inlet for receiving the perfusate returning from the cassette;
  an actuator having a forcing plate to provide an actuating force to a pump body of said pump by applying a pressure thereto, and to retreat away from the pump body to remove the actuating force from said pump body;
  said pump configured to provide a pulsatile pumping force to the perfusate via a pumping stroke in response to said actuating force, said pumping stroke followed by a return stroke;
  said pump comprising an internal cavity and an elbow configured to inhibit a passing of air bubbles from said internal cavity through said outlet;
  said pumping stroke comprising a pumping movement from a start position to an end position and said return stroke comprising a retreating movement from said end position to said start position;
  said pumping stroke causing said pump body to collapse to force a flow of the perfusate through said outlet to the organ, said pump body collapsing in a direction of the flow of the perfusate;

said actuator coupled to said pump such that said actuator retreats away from said pump body to remove the actuating force from said pump body during said retreating movement;

said pump body being sufficiently resilient such that said pump body expands in a direction toward the retreating forcing plate during said retreating movement; and said return stroke allowing the perfusate to enter said pump through said inlet of said pump while avoiding sending the perfusate through said outlet.

* * * * *